United States Patent
Jordan

(10) Patent No.: US 11,554,267 B2
(45) Date of Patent: Jan. 17, 2023

(54) SYSTEMS AND METHODS FOR DELIVERING THERAPEUTIC AGENTS TO THE BRAIN USING TMS

(71) Applicant: Synaptec Network, Inc., Santa Monica, CA (US)

(72) Inventor: Sheldon Jordan, Pacific Palisades, CA (US)

(73) Assignee: SYNAPTEC NETWORK, INC., Santa Monica, CA (US)

( * ) Notice: Subject to any disclaimer, the term of this patent is extended or adjusted under 35 U.S.C. 154(b) by 288 days.

(21) Appl. No.: 16/590,923

(22) Filed: Oct. 2, 2019

(65) Prior Publication Data

US 2020/0108263 A1 Apr. 9, 2020

Related U.S. Application Data

(60) Provisional application No. 62/741,667, filed on Oct. 5, 2018.

(51) Int. Cl.
*A61N 2/00* (2006.01)

(52) U.S. Cl.
CPC ................................... *A61N 2/002* (2013.01)

(58) Field of Classification Search
CPC . A61N 2/002; A61N 2/006; A61F 2007/0002; A61F 7/12; A61K 47/46; A61K 41/0052
See application file for complete search history.

(56) References Cited

U.S. PATENT DOCUMENTS

| 6,514,221 | B2 | 2/2003 | Hynynen et al. |
| 9,636,517 | B2 * | 5/2017 | Pell .......................... A61N 2/02 |
| 10,285,934 | B1 * | 5/2019 | Sharma ................ A61K 9/0085 |
| 2009/0004475 | A1 * | 1/2009 | Sadaka ................. H01F 1/0054 427/130 |
| 2009/0131739 | A1 | 5/2009 | Shalev |
| 2009/0285885 | A1 * | 11/2009 | Chen .................... A61K 9/5192 424/451 |
| 2011/0213193 | A1 | 9/2011 | Nair |

(Continued)

FOREIGN PATENT DOCUMENTS

WO 2013170379 11/2013

OTHER PUBLICATIONS

International Search Report dated Jan. 29, 2020, for PCT Application Serial No. PCT/US2019/054212, filed Oct. 5, 2018. 5 pages.

(Continued)

*Primary Examiner* — Samuel G Gilbert
(74) *Attorney, Agent, or Firm* — Fish IP Law, LLP

(57) ABSTRACT

The improvement of administration of a therapeutic agent to a targeted region of a patient's brain is herein described. A magnetic material, preferably soluble iron, is administered to the patient. A magnetic field, for example via transcranial magnetic stimulation (TMS), is applied to the targeted region of the patient's brain. The magnetic field is used to agitate magnetic material localized to the targeted region of the brain, temporarily forming openings in the blood-brain barrier (BBB), increasing local perfusion, or both at the targeted region. A therapeutic agent is administered to the patient and is delivered to the targeted region of the patient's brain through openings in the BBB, local perfusion, or both.

15 Claims, 3 Drawing Sheets

(56) References Cited

U.S. PATENT DOCUMENTS

| | | |
|---|---|---|
| 2013/0317279 A1 | 11/2013 | Khizroev |
| 2015/0126964 A1* | 5/2015 | Martel ............... A61K 41/0052 |
| | | 604/507 |
| 2016/0287856 A1 | 10/2016 | Konofagou et al. |
| 2018/0015047 A1* | 1/2018 | Black .................... A61B 18/12 |

OTHER PUBLICATIONS

Burgess et al., Targeted Delivery of Neural Stem Cells to the Brain Using MRI-Guided Focused Ultrasound to Disrupt the Blood Brain Barrier, Plos One, Nov. 2011, vol. 6, Issue 11, Nov. 16, 2011.

Sheikov et al., Cellular Mechanisms of the Blood-Brain Barrier Opening Induced by Ultrasound in Presence of Microbubbles, Elsevier, Ultrasound in Med. & Biol., vol. 30, No. 7, pp. 979-989, 2004.

Kinashita, et al., Noninvasive Localized Delivery of Herceptin to the Mouse Brain by MRI-Guided Focused Ultrasound-Induced Blood-Brain Barrier Disruption, PNAS, vol. 103, No. 13, Aug. 2006, pp. 11719-11723.

\* cited by examiner

SYSTEMS AND METHODS FOR DELIVERING THERAPEUTIC AGENTS TO THE BRAIN USING TMS

This application claims priority to U.S. provisional application 62/741,667, filed Oct. 5, 2018, the disclosure of which is incorporated herein by reference.

FIELD OF THE INVENTION

The field of the invention is methods, systems, kits, and devices related to delivering therapeutic agents to the brain.

BACKGROUND

The background description includes information that may be useful in understanding the present invention. It is not an admission that any of the information provided herein is prior art or relevant to the presently claimed invention, or that any publication specifically or implicitly referenced is prior art.

In some cases, the most desirable way to treat an ailment is to treat the source. However, for treatment of ailments in or relating to regions of the brain, the blood-brain barrier (BBB) often hinders treatment by preventing diffusion of therapeutic agents into the brain. While it is known to mechanically bypass the BBB, for example through use of a needle to inject therapeutic agents directly into the brain, such methods are undesirable due to damage caused by such invasive methods.

Non-invasive methods have been developed to apply targeted therapies to various regions of the brain. For example, it is known to perform transcranial magnetic stimulation (TMS) of targeted regions of the brain by applying a magnetic field to the targeted region to cause electric current to flow in the targeted region of the brain via electromagnetic induction. While such treatments have proven effective at non-invasively treating depression, it is still desired to bring therapeutic agents in contact with targeted regions of the brain for treatment.

Methods of delivering therapeutic agents to regions of the brain have been developed. For example, "Targeted Delivery of Neural Stem Cells to the Brain Using MM-Guided Focused Ultrasound to Disrupt the Blood-Brain Barrier," PLoS ONE 6(11): e27877. doi:10.1371, by Burgess, et al. reports using Mill guided focused ultrasound with microbubbles to temporarily open targeted regions of the BBB to allow entry of neural stem cells in animal models. But it is also known that applying ultrasound and microbubbles to open the BBB can cause damage to the BBB and surrounding tissue, which can be permanent. See "Cellular Mechanisms Of The Blood-Brain Barrier Opening Induced By Ultrasound In Presence Of Microbubbles," Ultrasound in Med. & Biol., Vol. 30, No. 7, pp. 979-989, 2004 by Sheikov, et al; "Noninvasive Localized Delivery Of Herceptin To The Mouse Brain By Mri-Guided Focused Ultrasound-Induced Blood-Brain Barrier Disruption," PNAS, Vol. 103, No. 31, 11719-23 by Kinoshita, et al. Methods, systems, and devices are still needed to deliver therapeutic agents across the BBB without causing damage to the BBB and surrounding material, for example to safely and temporarily open the BBB or increase perfusion.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Thus, there remains a need for systems and methods for delivering therapeutic agents to the brain in humans.

SUMMARY OF THE INVENTION

The inventive subject matter provides apparatus, systems, and methods for delivering a therapeutic agent to a patient's brain, preferably a human. A solution containing a magnetic material is administered to a patient's blood stream. A magnetic field is then applied to a targeted region of the patient's brain. The magnetic field is used to affect the magnetic material at the targeted region of the brain to facilitate delivery of the therapeutic agent to the brain at the targeted region, for example by opening the BBB, increasing local perfusion, or combinations thereof. The therapeutic agent is administered to the patient's blood stream, preferably after affecting the magnetic material, and the therapeutic agent is preferentially delivered to the targeted region in the brain. In preferred embodiments, the therapeutic agent is administered after the BBB has been opened, or after local perfusion is increased, and in some cases after both have occurred.

DETAILED DESCRIPTION

Figure 1:
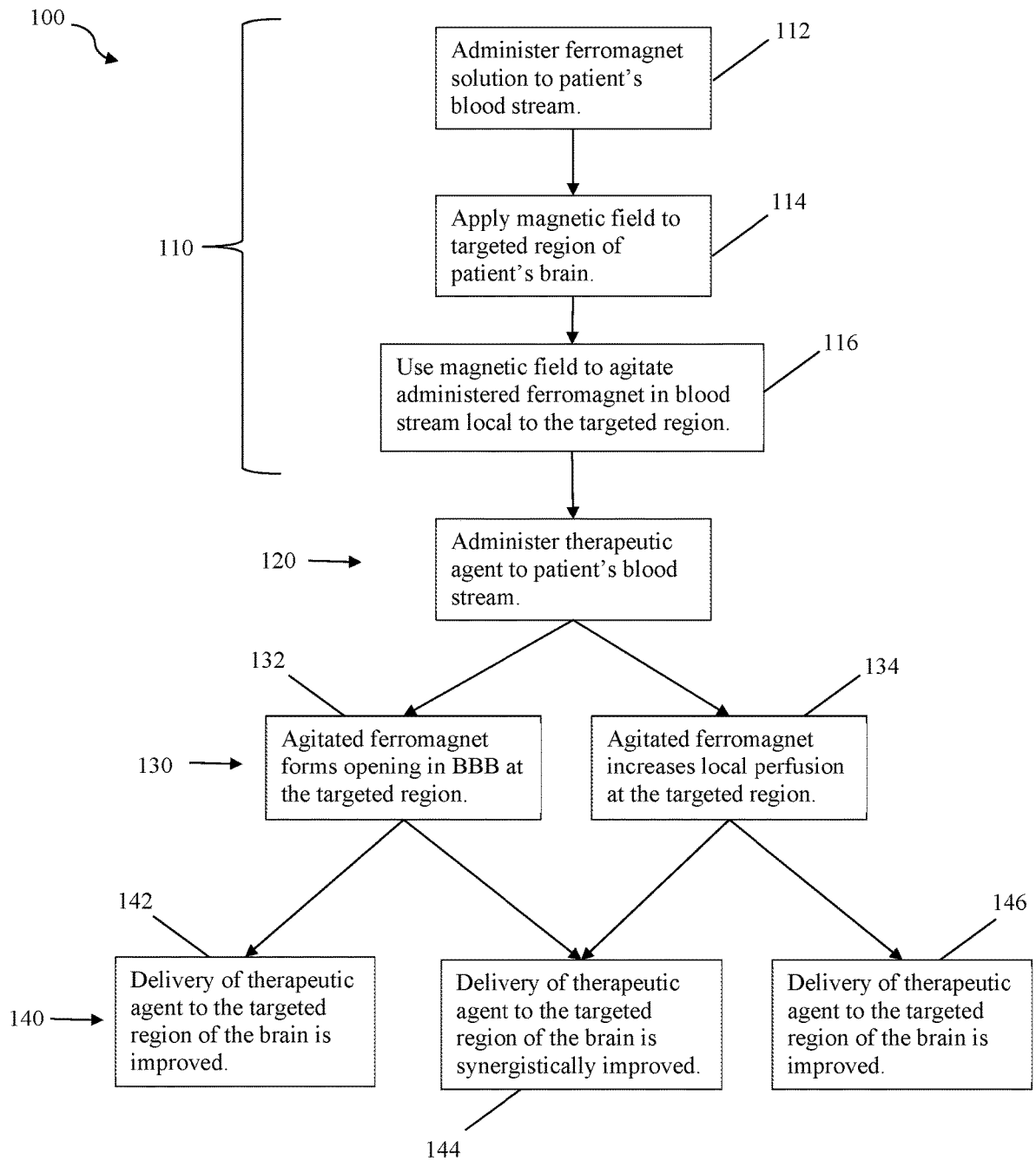
FIG. 1 shows a flow chart of a method of the inventive subject matter.

The inventive subject matter provides apparatus, systems, and methods for delivering a therapeutic agent to a patient's brain, preferably a human. A solution containing a magnetic material (e.g., ferromagnet (e.g., soluble iron, nickel, cobalt, alnico, etc.), ferrimagnet, paramagnet (e.g., aluminum, titanium, etc.) is administered to a patient's blood stream (e.g., intravenous injection, intravenous infusion, local to the heart, via PICC line, orally, etc.). A magnetic field is then applied to a targeted region of the patient's brain, typically via a transcranial magnetic stimulation (TMS) device. The magnetic field is used to affect the magnetic material (e.g., vibrate, spin, translate, combination thereof, etc.) at the targeted region of the brain to facilitate delivery of the therapeutic agent to the brain at the targeted region, for example by opening the BBB (preferably temporarily, e.g. less than 60, 45, 30, 25, 20, 15, 10, or less than 5 minutes), increasing local perfusion (preferably temporarily, e.g. less than 60, 45, 30, 25, 20, 15, 10, or less than 5 minutes), etc.

The therapeutic agent is administered to the patient's blood stream (e.g., intravenous injection, intravenous infusion, local to the heart, via PICC line, orally, etc.), preferably after affecting the magnetic material, and the therapeutic agent is preferentially delivered to the targeted region in the brain. In preferred embodiments, the therapeutic agent is administered after the BBB has been opened, or after local perfusion is increased, and in some cases after both have occurred. In some embodiments, the therapeutic agent is administered to the patient along with the magnetic material, after which the magnetic field is applied to the targeted region of the brain. It is also contemplated that, after the magnetic material and therapeutic material are administered to the patient, the magnetic field is applied in a cyclic pattern to temporarily open the BBB or increase local perfusion (e.g., open for less than 5, 4, 3, 2, or 1 min), for example by applying the magnetic field for periods of less than 10 or 5 minutes, followed by a break of less than 20 or 10 minutes.

The region of the patient's brain to be targeted is preferably associated with a disease condition. In some embodiments, the disease condition is associated with at least one of a learning disorder, an anxiety disorder, a motor disorder, a consciousness disorder, a movement disorder, an attention disorder, a stroke, a vascular disease, dementia, progressive dementia, Alzheimer's disease, Parkinson's disease, multiple sclerosis, cancer, schizophrenia, depression, developmental disorder, substance abuse, and traumatic brain injury. However, any disease or disease condition that is pathologically associated with a region of the brain is appropriate for the contemplated methods. For example, the targeted region of the patient's brain can be the frontal lobe, parietal lobe, occipital lobe, temporal lobe, hippocampus, hypothalamus, brain stem, cerebellum amygdala, corticospinal tract, thalamus, substantia nigra, basal ganglia, a tumor, a lesion, necrotic tissue, Heschl's gyms, Brodmann area 25, a point of injury, combinations thereof, or any other region of interest. In some embodiments more than one region of the brain is targeted, for example to treat more than one disease, to combat a disease associated with more than one region of the brain, or to synergistically improve treatment outcome.

In some embodiments, the therapeutic agent is a chemical, a molecule, a drug (e.g., chemo agent etc), or a biological product (e.g., proteomic material, genomic material, transcriptomic material, vesicle, exosome, stem cell, etc). The therapeutic agents can be derived naturally (e.g., extracted from natural biological process), engineered (e.g., extracted from engineered biological process), synthetically (e.g., in vitro), or some combination thereof. Likewise, in some embodiments it is favorable to deliver more than one therapeutic agent to the brain across the BBB of the patient, in some cases delivering multiple therapeutic agents of the same or different types or derivations. The therapeutic agents can also be delivered via a carrier (e.g., liposomal, viral, exosomal, etc.), whether natural, engineered, or synthetic.

The magnetic material is typically suspended in a solution (e.g., saline) and injected intravenously into the patient's blood stream. The magnetic material is typically nano-scale (e.g., less than 500 nm, 200 nm, 100 nm, 50 nm, 10 nm, 5 nm, or less than 1 nm, etc) but can also be micro-scale or larger. The magnetic material is typically a material, metal, or alloy that has a magnetic moment (e.g., Co, Fe, $Fe_2O_3$, $FeOFe_2O_3$, $NiOFe_2O_3$, $CuOFe_2O_3$, $MgOFe_2O_3$, MnBi, Ni, MnSb, $MnOFe_2O_3$, $Y_3Fe_5O_{12}$, $CrO_2$, MnAs, Gd, Tb, Dy, EuO, alloys thereof, etc.). Preferably a plurality (e.g., more than 1,000, more than 10,000, more than 100,000) of magnetic materials are administered to the patient's blood stream, whether of the same or different types, sizes, relative number, or relative concentration. Viewed from another perspective, an amount of magnetic material (e.g., particles) are administered to the patient such that a concentration of magnetic material in the blood stream in a targeted region of the brain is sufficient to facilitate delivery of therapeutic agents across the BBB when a magnetic field is applied to the targeted region.

The magnetic field is preferably applied using a TMS device, though any appropriate system or device for generating or applying a magnetic field is contemplated. Typically, the magnetic material is affected for at least 30 seconds or 1 minute, though the magnetic field can affect the magnetic material for at least 10 minutes, 20 minutes, 30 minutes, 45 minutes, or more than 60 minutes. The magnetic field can optionally be applied constantly or in pulses of 1 second, 5 seconds, 10 seconds, or more than 30 seconds. In some embodiments, therapeutic agents are administered to the patient's blood stream before, after, during application of the magnetic field, or some combination thereof. It is further contemplated that the magnetic field is selectively applied to primarily or selectively to the magnetic material, applied more broadly to affect the targeted region of the brain, or combinations thereof.

Likewise, more than one magnetic field can be applied to the same region of the brain or to multiple regions of the brain (preferably with precision), whether simultaneously, alternating, in series, in cascade, or some combination thereof. For example, a base or low intensity magnetic field may be applied generally to the patient's brain or a portion of the brain (e.g., hemisphere, lobe, cortex, etc.) while one or more smaller, localized magnetic fields are applied to specific regions of the patient's brain (e.g., less than 5 cm, 4 cm, 3 cm, 2 cm, or less than 1 cm cross section, etc.), for example the specific targeted regions It is contemplated that the inventive subject matter improves delivery of therapeutic agents to targeted regions of the patient's brain, preferably selectively or substantially exclusively to the targeted regions. Embodiments of the inventive subject matter improve delivery of therapeutic agents to targeted regions of the brain by as much as 30%, 40%, 50%, 60%, 70%, 80%, 90%, 100%, or more than 200% compared to administration of the therapeutics without applying a magnetic field or administering magnetic material to the patient. Similarly, the inventive subject matter improves therapeutic outcome of the patient by more than 30%, 40%, 50%, 60%, 70%, 80%, 90%, 100%, or more than 200% compared to administration of the therapeutics without applying a magnetic field or administering magnetic material to the patient Therapeutic methods and methods of treating a patient by using a TMS device to facilitate delivery of a therapeutic agent to a patient's brain through the BBB are also contemplated. The TMS device is used to affect a ferromagnet (or other magnetic material) located in a targeted region of the patient's brain. Affecting the ferromagnet (e.g., vibrate, spin, translate, etc) within the targeted region opens the patient's BBB in the targeted region, increases local perfusion in the region, or some combination thereof. A therapeutic agent is administered to the patient, whether before, during, or after use of the TMS device.

Typically, the procedure for applying TMS with an intravenous soluble iron solution involves giving an iron containing solution to the patient intravenously and performing TMS over a region of the patient's brain that is of therapeutic interest. Appropriate commercially available iron containing solutions are known in the art and are available with FDA approval. It is contemplated that TMS is applied with a standard FDA approved device. The TMS interacts with the soluble iron in a manner that increases perfusion of the BBB, forms an opening in the BBB, or both.

Viewed from another perspective, iron particles interact with the TMS magnetic field in such a way that perfusion or BBB opening is effected in a targeted, regionally specific manner of the brain which allows the therapeutic agent (e.g., molecule, drug, etc.) to cross the BBB into the brain in that targeted region. It is contemplated that such methods are applicable for delivery of medications, small molecules, or biological products (e.g. exosomes and stem cells) to treat a host of diagnoses, both psychiatric and neurological.

While it is contemplated the inventive subject matter is applicable to any condition (e.g., disease, disorder, characteristic, etc) and region of the brain, preferred conditions and regions of the brain include those listed in Table 1.

TABLE 1

| Condition | Region of the Brain |
| --- | --- |
| Alzheimer's disease: | Hippocampus and surrounding cortex |
| Parkinson's disease: | Substantia nigra and basal ganglia |
| Vascular dementia: | Diffusely throughout the brain |
| MS: | Proximal to MS lesions |
| Cancer: | Proximal to tumor and necrotic tissue |
| Schizophrenia: | Frontal lobe and Heschl's gyrus |
| Depression: | Frontal lobe and Brodmann area 25 |
| Substance abuse: | Diffusely throughout the cortex but likely not in subcortical structures |
| Traumatic Brain Injury: | Proximal to area of injury |

FIG. 1 depicts flow chart 100 for embodiments of improving delivery of a therapeutic agent to a targeted region of a patient's brain, including preparation steps 110, administration step 120, agitation steps 130, and delivery steps 140. Preparation steps 110 include step 112 for administering a ferromagnet solution (e.g., soluble iron) to the patient's blood stream, followed by step 114 for applying a magnetic field to the targeted region of the patient's brain. Next, step 116 uses the magnetic field (preferably via TMS) to agitate ferromagnets that have been administered to the patient and are in the blood stream near (more preferably selectively at) the targeted region of the patient's brain (or at more than one targeted region). In some embodiments, the ferromagnet solution of step 112 and the magnetic field of step 114 are administered/applied at least partially simultaneously. For example, step 112 administers the ferromagnet solution while step 114 applies the magnetic field, and once the desired amount of ferromagnet solution has been administered, step 112 ends while step 114 continues to apply the magnetic field to the target region of the brain.

Administration step 120 next administers the therapeutic agent to the patient's blood stream, followed by agitation steps 130. In step 132, ferromagnets agitated by the magnetic field form openings in the BBB proximal to (preferably selectively at) the targeted region, while in step 134, the agitated ferromagnets increase local perfusion proximal (preferably selectively at) the targeted regions. It is contemplated that parameters of the inventive method (e.g., amount of ferromagnet used, concentration of ferromagnet, composition of ferromagnet, size of ferromagnet particle(s), size of magnetic field, intensity of magnetic field, etc.) can be selectively adjusted such that either step 132 or step 134 occur, or both, whether simultaneously, partially overlapping, or alternating, etc., and at one or more targeted regions of the patient's brain. Delivery steps 140 occur after both, or either, of steps 132 and 134. Step 142 occurs only when step 132 has opened the BBB at the targeted region, while step 146 occurs only when step 134 has increased local perfusion at the targeted region, in both cases improving delivery of the therapeutic agent to the targeted region of the brain. Step 144 occurs when both step 132 and step 134 occur, both opening the BBB and increasing local perfusion, leading to a synergistic improvement of delivery of the therapeutic agent to the targeted region of the brain.

Figure 2:
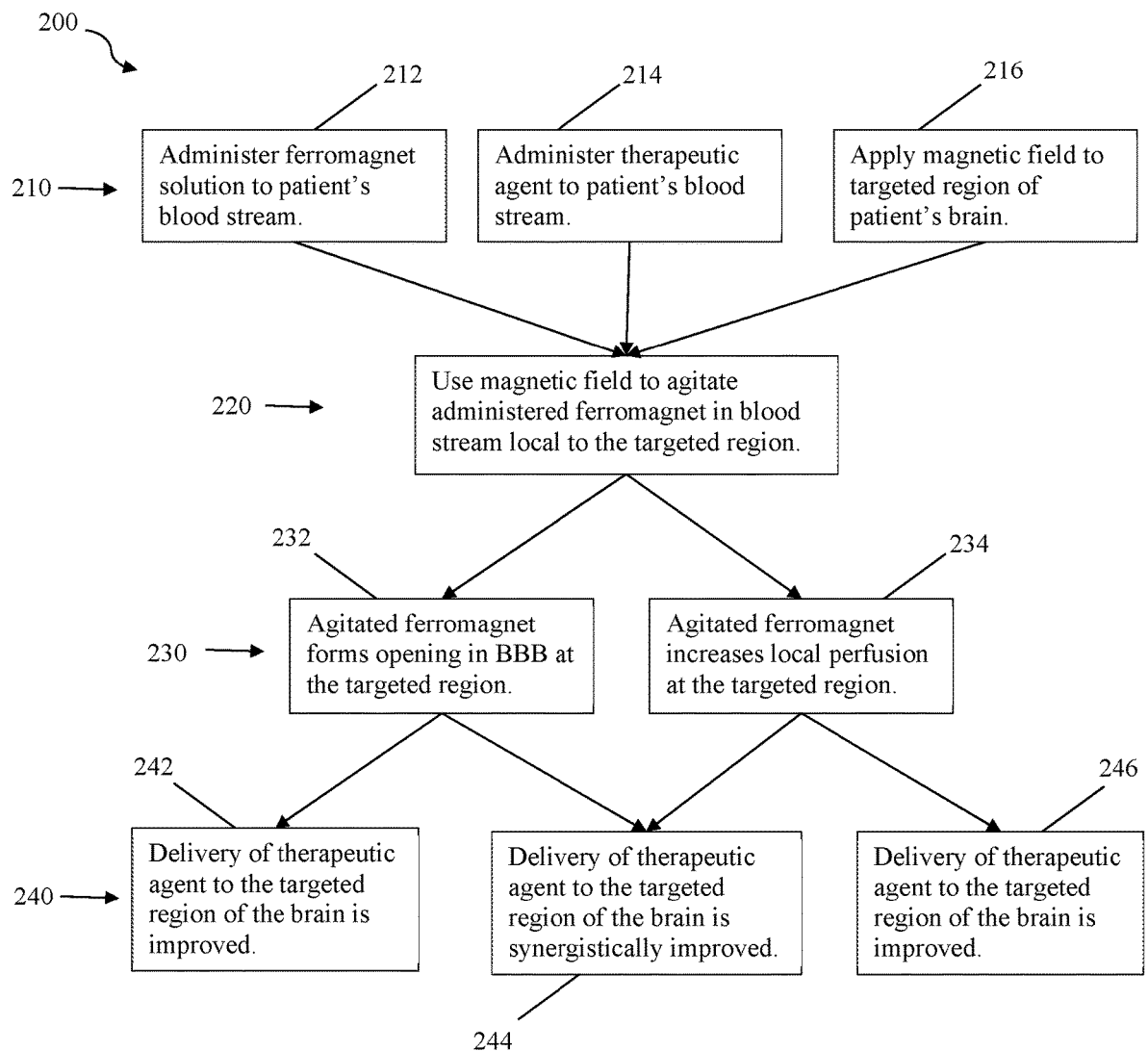
FIG. 2 shows another flow chart of a method of the inventive subject matter.

FIG. 2 depicts flow chart 200 of further embodiments for improving delivery of a therapeutic agent to a targeted region of a patient's brain, including preparation steps 210, magnetation step 220, agitation steps 230, and delivery steps 240. Preparation steps 210 include step 212 for administering a ferromagnet solution to the patient's blood stream, step 214 for administering a therapeutic agent to the patients' blood stream, and step 216 for applying a magnetic field to a targeted region of the patient's brain (in some embodiments more than one targeted region), which occur substantially simultaneously. In some embodiments, steps 212, 214, and 216 are applied at least partially simultaneously or overlapping. For example, each step can be initiated at the same time, and the magnetic field of step 216 continues to be applied after the ferromagnet solution of step 212 and the therapeutic agent of step 214 have been administered. In other embodiments, the ferromagnet solution of step 212 is administered first, the therapeutic agent of step 214 is then administered while the ferromagnet solution of step 212 is administered, and the magnetic field of step 216 is applied, after which steps 212 and 214 end, either simultaneously or one after the other.

Magnetation step 220 occurs after (or partially simultaneous with step 216) preparation steps 210, and uses the magnetic field to agitate ferromagnets in the patient's blood stream local to (preferably selectively at) the targeted region of the patient's brain, followed by agitation steps 230 and delivery steps 240. Agitation steps 230 and delivery steps 240 are substantially as described above for agitation steps 130 and delivery steps 140.

Figure 3:
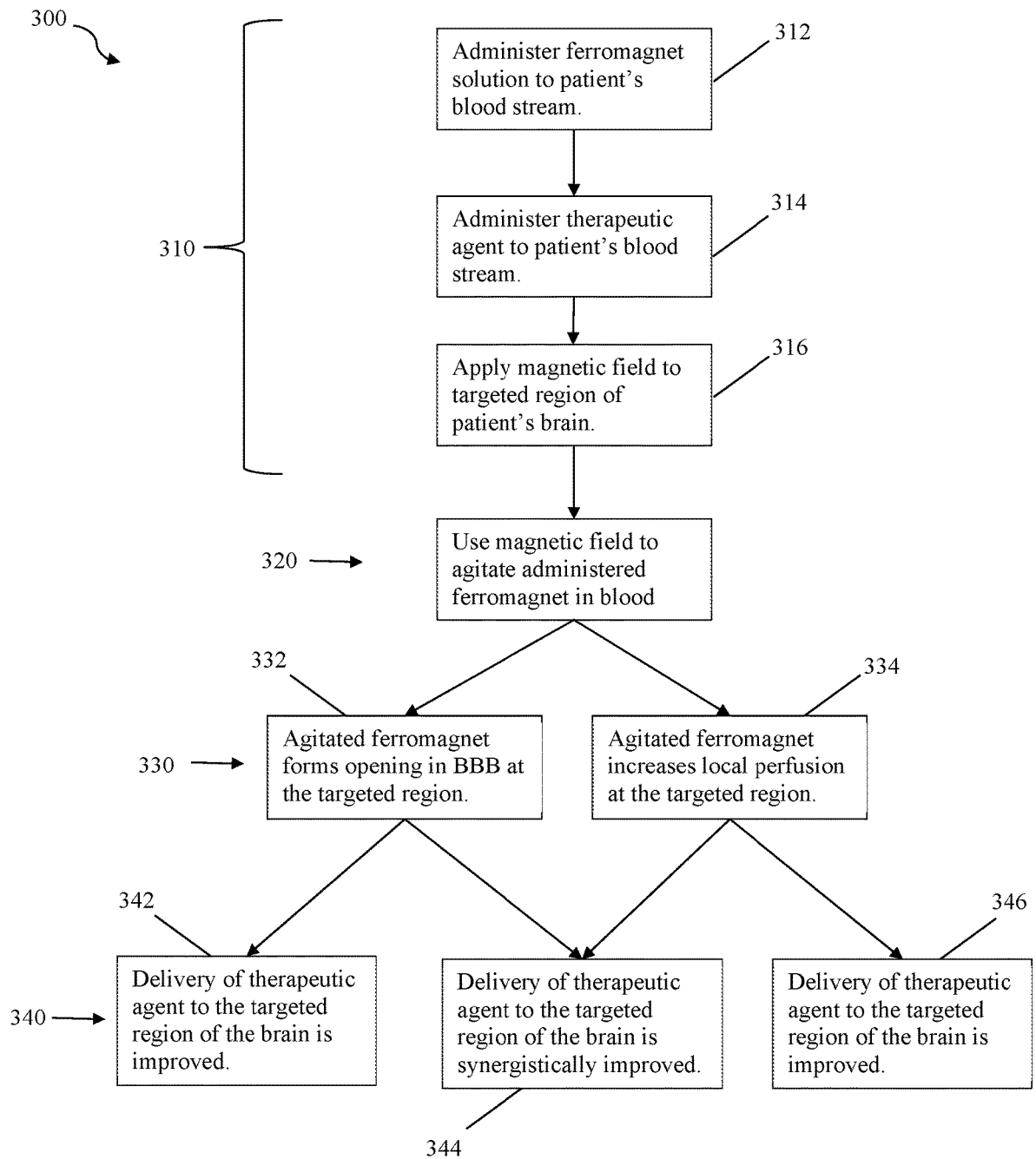
FIG. 3 shows yet another flow chart of a method of the inventive subject matter.

FIG. 3 depicts flow chart 300 of yet further embodiments for improving delivery of a therapeutic agent to a targeted region of a patient's brain, including preparation steps 310, magnetation step 320, agitation steps 330, and delivery steps 340. Preparation steps 310 include step 312 administering a ferromagnet solution to the patient's blood stream, followed by step 314 administering a therapeutic agent to the patient's blood stream. Next step 316 applies a magnetic field to a targeted region of the patient's brain. In some embodiments, the ferromagnet solution of step 312 and the therapeutic agent of step 314 are administered/applied at least partially simultaneously. For example, the ferromagnet solution is administered while the therapeutic agent is administered, and therapeutic agent continues to be administered after step 312 ends.

Magnetation step 320 occurs after (or partially simultaneous with step 316) preparation steps 310, and uses the magnetic field to agitate ferromagnets in the patient's blood stream local to (preferably selectively at) the targeted region of the patient's brain, followed by agitation steps 330 and delivery steps 340. Agitation steps 330 and delivery steps 340 are substantially as described above for agitation steps 130 and delivery steps 140.

Various objects, features, aspects, and advantages of the inventive subject matter will become more apparent from the following detailed description of preferred embodiments, along with the accompanying drawing figures in which like numerals represent like components.

The inventive subject matter provides apparatus, systems, and methods for comparative analysis of tissue and organ scans between patients or groups of patients without sensitivity to patient-specific or scanner specific characteristics, including prediction, diagnosis, prognosis, tracking, and treatment guidance.

The following description includes information that may be useful in understanding the present invention. It is not an admission that any of the information provided herein is prior art, necessary, or relevant to the presently claimed invention, or that any publication specifically or implicitly referenced is prior art.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification or claims refers to at least one of something selected from the group consisting of A, B, C . . . and N, the text should be interpreted as requiring only one element from the group, not A plus N, or B plus N, etc.

What is claimed is:

1. A method of delivering a therapeutic agent to a patient's brain, comprising:
    administering a solution containing a ferromagnet to a patient's blood stream, wherein the solution contains a plurality of ferromagnets comprising ferromagnets of more than one type of material;
    applying a magnetic field to a targeted region of the patient's brain;
    affecting the ferromagnet with the magnetic field at the targeted region to facilitate delivery of the therapeutic agent to the patient's brain; and
    administering the therapeutic agent to the patient's blood stream, wherein the therapeutic agent enters the patient's brain at the targeted region;
    wherein the step of administering the solution containing the ferromagnet and applying the magnetic field to the targeted region at least partially overlap.

2. The method of claim 1, wherein the step of affecting the ferromagnet with the magnetic field forms an opening in a blood-brain barrier (BBB) at the targeted region.

3. The method of claim 2, wherein the step of administering the therapeutic agent occurs separately from the step of administering the solution containing the ferromagnet to the patient's blood stream.

4. The method of claim 2, wherein opening the BBB is temporary.

5. The method of claim 1, wherein the targeted region of the patient's brain is associated with a disease condition.

6. The method of claim 5, wherein the disease condition is associated with a disease selected from the group consisting of a learning disorder, an anxiety disorder, a motor disorder, a consciousness disorder, a movement disorder, an attention disorder, a stroke, a vascular disease, dementia, progressive dementia, Alzheimer's disease, Parkinson's disease, multiple sclerosis, cancer, schizophrenia, depression, developmental disorder, substance abuse, and traumatic brain injury.

7. The method of claim 1, wherein the targeted region of the patient's brain is selected from the group consisting of frontal lobe, parietal lobe, occipital lobe, temporal lobe, hippocampus, hypothalamus, brain stem, cerebellum, amygdala, corticospinal tract, thalamus, substantia nigra, basal ganglia, and Heschl's gyrus.

8. The method of claim 1, wherein the therapeutic agent is selected from the group consisting of a chemical, a molecule, or a biological product.

9. The method of claim 1, further comprising administering a plurality of therapeutic agents comprising therapeutic agents of more than one type or derivation, wherein the plurality of therapeutic agents are selected from the group consisting of a chemical, a molecule, a drug, or a biological product.

10. The method of claim 1, wherein the therapeutic agent selected from the group consisting of a chemical, a molecule, a drug, or a biological product, is synthetic.

11. The method of claim 1, wherein the ferromagnet is selected from the group consisting of $FeOFe_2O_3$, $NiOFe_2O_3$, $CuOFe_2O_3$, $MgOFe_2O_3$, MnBi, $MnOFe_2O_3$, $Y_3Fe_5O_{12}$, $CrO_2$, MnAs, Gd, Tb, Dy, EuO, and alloys thereof.

12. The method of claim 1, wherein the targeted region of the patient's brain is of therapeutic interest.

13. The method of claim 1, wherein the step of affecting the ferromagnet with the magnetic field is performed continuously between 30 seconds and 20 minutes.

14. The method of claim 1, wherein the magnetic field is applied using a transcranial magnetic stimulation (TMS) device.

15. The method of claim 1, further comprising a step of applying a second magnetic field to affect a second ferromagnet located at a second targeted region of the patient's brain.

* * * * *

UNITED STATES PATENT AND TRADEMARK OFFICE
CERTIFICATE OF CORRECTION

| | |
|---|---|
| PATENT NO. | : 11,554,267 B2 |
| APPLICATION NO. | : 16/590923 |
| DATED | : January 17, 2023 |
| INVENTOR(S) | : Sheldon Jordan |

It is certified that error appears in the above-identified patent and that said Letters Patent is hereby corrected as shown below:

In the Claims

At Column 8, Line 66, in Claim 11, change "$MgOFe_2O_3$, MnBi, $MnOFe_2O3$" to --$MgOFe_2O_3$, MnBi, MnSb, $MnOFe_2O_3$--

Signed and Sealed this
Seventh Day of March, 2023

Katherine Kelly Vidal
*Director of the United States Patent and Trademark Office*